US00PP11775P2

(12) United States Plant Patent
Zary

(10) Patent No.: US PP11,775 P2
(45) Date of Patent: Feb. 13, 2001

(54) HYBRID TEA ROSE PLANT NAMED 'JACAVIRT'

(75) Inventor: Keith W. Zary, Thousand Oaks, CA (US)

(73) Assignee: Jackson & Perkins Wholesale, Inc., Medford, OR (US)

( * ) Notice: Under 35 U.S.C. 154(b), the term of this patent shall be extended for 0 days.

(21) Appl. No.: 09/234,792

(22) Filed: Jan. 20, 1999

(51) Int. Cl.[7] ..... A01H 5/00
(52) U.S. Cl. ..... Plt./140
(58) Field of Search ..... Plt./140, 139

(56) References Cited

PUBLICATIONS

UPOV–ROM, 1999/02, Plant Variety Database, GTI Jouve Retrieval Software, citation for 'JACavirt'.*

* cited by examiner

*Primary Examiner*—Howard J. Locker
(74) *Attorney, Agent, or Firm*—Klarquist Sparkman Campbell Leigh & Whinston, LLP

(57) ABSTRACT

Hybrid tea rose plant having a deep red flower; large bud; glossy, disease resistant foliage; and strong, upright growth.

1 Drawing Sheet

The present invention relates to a new and distinct variety of rose plant of the hybrid tea rose class which was originated by me by crossing the variety 'JACsay', unpatented ('Samantha'×'Royalty'), with the variety 'PEKcoujenny', U.S. Plant Pat. No. 7,749.

The primary objective of this breeding was to produce a deep red flower and large bud of the female parent combined with the glossy, disease resistant foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Large bud;
2. Deep red and open flower;
3. Glossy, dark green foliage;
4. Resistant to powdery mildew; and
5. Strong, upright, vigorous growth.

'JACavirt' was bred to be a greenhouse cut rose variety. It produces 170–180 stems/m$^2$ of greenhouse with average stem length of 22–26 inches. Vase life is long at twelve days.

Asexual reproduction of this new variety by budding on Manetti rootstalk, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'JACsay' (unpatented ('Samantha'× 'Royalty')).

*Pollen parent.*—'PEKcoujenny' (U.S. Plant Pat. No. 7,749).

Classification:

*Botanical.*—*Rosa hybrida.*

*Commercial.*—Hybrid Tea.

FLOWER

Observations made from specimens grown in a greenhouse environment at Somis, Calif., February 1997 to December 1998.

Blooming habit: Continuous.

Bud:

*Size.*—Two and one-quarter inches long when the petals start to unfurl.

*Form.*—The bud form is long, pointed ovoid.

*Color.*—When sepals first divide, bud color is Red Group 53B with petal edges as they unfurl showing Greyed-Purple Group 187A. When half blown, the upper sides of the petals are Red Group 46A with the outer most petal edges showing Greyed-Purple Group 187A. The lower sides of the petals are Red Group 53C.

*Sepals.*—Color: Green Group 138B. Surface texture: Covered in fine hairs. There are three normally to heavily appendaged sepals. There are two unappendaged sepals with hairy edges.

*Receptable.*—Color: Yellow-Green Group 146C. Shape: Funnel. Size: Large, about ⅝"×½". Surface: Smooth.

*Peduncle.*—Length: Very Long, averaging about six inches to six and one-half inches. Surface: Many small prickles. Color: Yellow-Green Group 146B. Strength: Stiff, erect.

Bloom:

*Size.*—Large. Average open size is five inches.

*Borne.*—Singly.

*Stems.*—Strength: Strong. Average length is about twenty-two to twenty-six inches.

*Form.*—When first open: High-centered. Permanence: Retains its form to the end, outer petals curl back.

*Petalage.*—Number of petals under normal conditions: 30.

*Color.*—The upper sides of the petals Red Group 46A with outer most petal edges showing Greyed-Purple Group 187A. The reverse sides of the petals are Red Group 53C. The base of each petal, on the upper surface, has a distinctive, 3/16"×3/16", Yellow Group 7C color spot. The lower surface has a 1/8"×1/8" Green-Yellow Group 1C color spot. The major color on the upper side is Red Group 46A.

*Variegations.*—There is an occasional whitish streak along the midrib on the guard petals.

*Discoloration.*—The general tonality at the end of the first day: No change. At the end of the third day: No change. By day ten in the vase, there is a change on the upper surface of the petal from Red Group 46A to Red Group 53C. Petal fall is day thirteen or fourteen.

*Fragrance.*—Slight.

Petals:

*Texture.*—Thick.

*Shape.*—Round.

*Form.*—Tips slightly recurved.

*Arrangement.*—Imbricated. Petaloids in the center are few. They are very similar in color to the petals and range from 1/2" to 3/4" long and 1/4" to 3/8" wide. They number from zero to four in ten flowers examined.

*Persistence.*—Petals drop off cleanly before drying.

*Lastingness.*—On the plant: Long (seven to eight days). As a cut flower: Long (about twelve days).

Reproductive parts:

*Anthers.*—Size: Large. Quantity: Many. Color: Yellow-Orange Group 18C. Arrangement: Regular around styles.

*Filaments.*—Color: Yellow Group 6C with some red coloration near the tip of the filament.

*Pollen.*—Color: Yellow-Orange Group 22C.

*Styles.*—Color: Red-Purple Group 59B.

*Stigmas.*—Color: Yellow-White Group 158B.

Plant:

*Form.*—Bush.

*Growth.*—Very vigorous, upright, branching. Mature plant height is about six to six and one-half feet, width is about four to four and one-half feet.

Foliage: Number of leaflets on normal mid-stem leaves: Five or seven.

*Size.*—Very large (7" long×5½" wide).

*Quantity.*—Abundant.

*Color.*—New foliage: Upper and lower surfaces: Greyed-Red Group 178A. Old foliage: Upper surface: Green Group 139A. Lower surface: Green Group 137C.

Leaflets:

*Shape.*—Pointed oval.

*Texture.*—Leathery, glossy.

*Edge.*—Serrated.

*Serration.*—Single, small.

*Petiole rachis.*—Yellow-Green Group 147C with Greyed-Purple Group 183B on younger leaves on the upper surface of the petiole rachis.

*Petiole underside.*—Smooth.

*Stipules.*—Long (3/4"), serrated.

*Disease resistance.*—Resistant to mildew and rust under normal growing conditions in a greenhouse. Not tested for blackspot.

Wood:

*New wood.*—Color: Greyed-Orange Group 176A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium, hooked downward.

*Color when young.*—Greyed-Orange Group 176A.

*Color when mature.*—Greyed-Orange Group 165A.

Small prickles:

*Quantity.*—On main stalks: None. On laterals: None.

I claim:

1. A new and distinct variety of rose plant of the hybrid tea class, substantially as herein shown and described, characterized particularly by its deep red and open flower; large bud; glossy, dark green foliage; resistance to powdery mildew and rust; and strong upright growth.

* * * * *

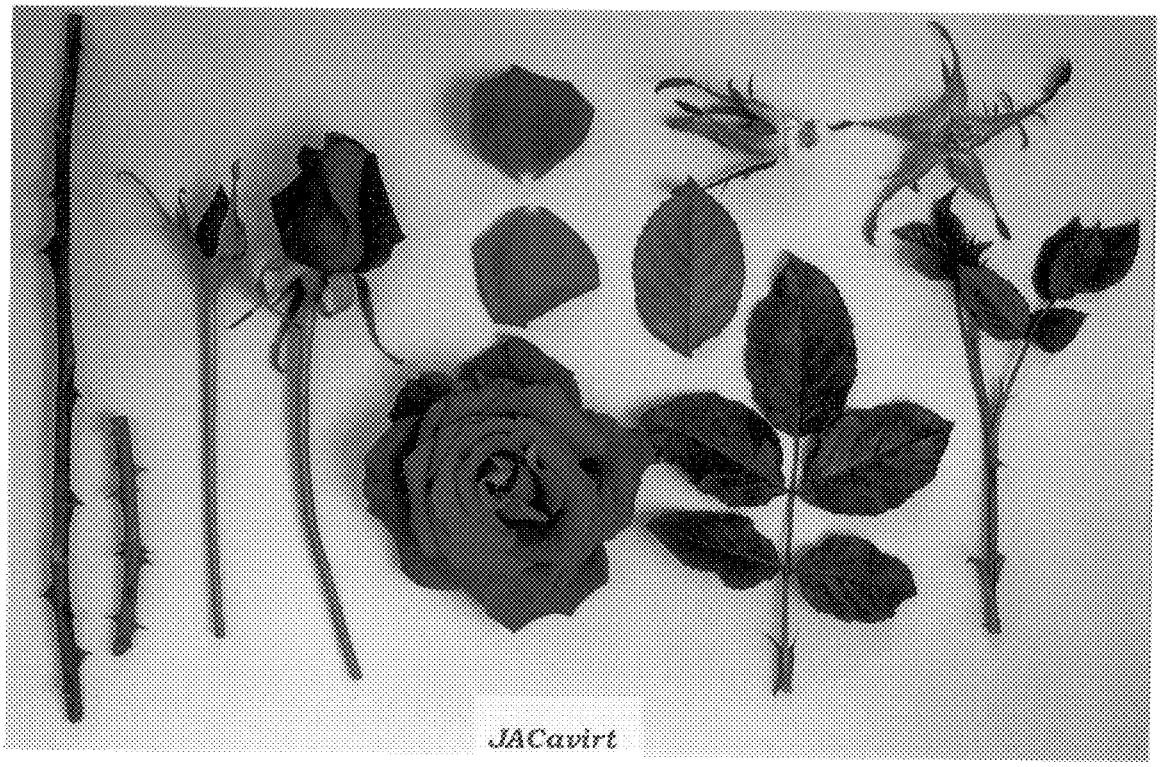
JACavirt